United States Patent [19]

Coates et al.

[11] Patent Number: 5,188,815
[45] Date of Patent: Feb. 23, 1993

[54] THERMOCHROMIC MIXTURES

[75] Inventors: David Coates; Ian C. Sage; John A. Jenner, all of Dorset, Great Britain

[73] Assignee: Merck Patent Gesellschaft mit Beschrankter Haftung, Darmstadt, Fed. Rep. of Germany

[21] Appl. No.: 424,264

[22] PCT Filed: Aug. 16, 1989

[86] PCT No.: PCT/EP89/00965
§ 371 Date: Oct. 4, 1989
§ 102(e) Date: Oct. 4, 1989

[87] PCT Pub. No.: WO90/02161
PCT Pub. Date: Mar. 8, 1990

[30] Foreign Application Priority Data

Aug. 31, 1988 [GB] United Kingdom ............ 8820581
Jan. 11, 1989 [GB] United Kingdom ............ 8900598

[51] Int. Cl.⁵ .............. A61K 49/00; A61K 7/021; A61K 7/035; C09K 19/34
[52] U.S. Cl. .................. 424/7.1; 424/63; 424/64; 424/69; 514/785; 514/788; 252/299.01; 252/299.61; 252/299.65; 252/299.67; 252/299.68
[58] Field of Search ............ 427/7.1; 424/1.1, 7.1, 424/63, 64, 69; 524/114; 430/40, 2; 252/299.61, 299.65, 299.68; 514/785, 788

[56] References Cited

U.S. PATENT DOCUMENTS

| | | | |
|---|---|---|---|
| 4,118,370 | 10/1978 | Sannes et al. | 260/45.75 |
| 4,448,727 | 5/1984 | Factor et al. | 260/463 |
| 4,880,560 | 11/1989 | Yoshinaga et al. | 252/299.01 |
| 5,116,527 | 5/1992 | Coates et al. | 252/299.61 |

FOREIGN PATENT DOCUMENTS

| | | |
|---|---|---|
| 211646 | 2/1987 | European Pat. Off. . |
| 213841 | 3/1987 | European Pat. Off. . |
| 309774 | 4/1989 | European Pat. Off. . |
| WO87/05017 | 8/1987 | Fed. Rep. of Germany . |
| WO89/02425 | 6/1988 | Fed. Rep. of Germany . |
| 58-103577 | 6/1983 | Japan . |

OTHER PUBLICATIONS

Patent Abstracts of Japan, vol. 7, No. 14, C146, abstract of JP57-170976, publ 1982.

Primary Examiner—Frederick E. Waddell
Assistant Examiner—T. J. Criares
Attorney, Agent, or Firm—Millen, White, Zelano and Branigan

[57] ABSTRACT

The invention relates to thermochromic liquid crystalline phases with at least two components, characterized in that at least one component is an optically active compound of the formula I

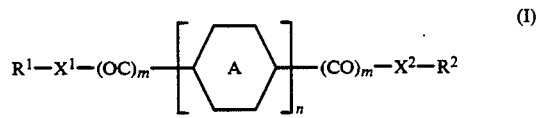

(I)

wherein
R¹ and R² are each independently a chiral residue, importing to the phase a tight helical twist.

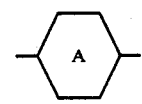

denotes a 1,4-phenylene group optionally substituted by fluorine,
X¹ and X² are each independently O or NH,
n is 1, 2 or 3 and
m is 0 or 1, which can be used in electro-optic devices, in temperature indicating devices or for color-changing cosmetics.

23 Claims, No Drawings

THERMOCHROMIC MIXTURES

SUMMARY OF THE INVENTION

The invention relates to thermochromic liquid crystalline phases with at least two components, characterized in that at least one component is an optically active compound of the formula I

wherein
$R^1$ and $R^2$ are each independently a chiral residue, imparting to the phase a tight helical twist,

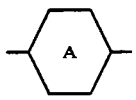

denotes a 1,4-phenylene group optionally substituted by fluorine,
$X^1$ and $X^2$ are each independently O or NH,
n is 1, 2, or 3 and
m is 0 or 1.

Liquid crystal phases are exhibited by certain organic compounds and constitute an intermediate state which exists between the crystalline solid and the fully disordered liquid phase and within which certain long range ordering of the molecules takes place.

There are two broad types of liquid crystal phase; the smectic mesophase in which the long range ordering is of a substantially lamellar type and the nematic mesophase in which the ordering is substantially linear, i.e., the molecules tend to line up with the long axes of the molecules parallel. Included sometimes as a subclass of the nematic mesophase and sometimes classified as a separate mesophase is the cholesteric mesophase. This last has a helical long range order imposed upon the linear order of the nematic mesophase. Compounds displaying a cholesteric mesophase are optically active (chiral) and the pitch of the helical twist is determined by the nature and extent of the optical activity. The pitch of the helical twist may be such that thin films of the cholesteric phase reflect visible light, resulting in the observation of bright colors, and the pitch may also be sharply temperature dependent resulting in the reflection of particular colors over particular temperature ranges so that the cholesteric mesophase in question can act as a "thermometer". This behavior is known as thermochromism.

The chiral compounds of the formula I induce a cholesteric mesophase (hereinafter designated Ch) because of their molecular shape and optical activity and also a chiral smectic C mesophase (hereinafter designated $S_c$) underlying the cholesteric mesophase to liquid crystalline phase which possess a nematic or a smectic C mesophase. They exhibit, either on their own or when mixed with one or more compounds capable of forming $S_c$ liquid crystal phases, a chiral $S_c$ liquid crystal phase in which the molecules lie tilted in the smectic layers which are themselves superimposed one upon the other to give a helical distribution of the tilt angles on passing through a stack of layers. A unique feature of the chiral $S_c$ mesophase of the phases of the present invention is that, in their planar $S_c$ textures, these mesophases have a helical pitch which gives a selective reflection of colored light of specific wavelengths which are dependent on temperature, i.e., the compounds are thermochromic.

The phases of the present invention exhibit, when mixed with one or more other liquid crystal compounds, a cholesteric liquid crystal phase in which the molecules are arranged in the helical formulation of that phase such that a film of the phase in the Grandjean plane texture rotates the plane of polarization of incident polarized light and reflects elliptically polarized light of specific wavelengths when illuminated by ordinary light, so that the mesophases are thermochromic.

The pitch of the cholesteric helix changes most abruptly in the temperature region close to a smectic phase, usually this is a smectic A or C phase. Hence thermochromic mixtures according to the invention are usually formulated such that they exhibit an underlying smectic phase so that the color change from blue (hot) to red (colder) occurs over a range of only few degrees (1-10° C.). However in some applications a temperature in-sensitive color is required and the smectic phase is depressed.

The phases of the present invention have properties such that they may be used in a liquid crystal electro-optic device such as a "phase change" device in which the material is changed between a so-called "focal-conic" cholesteric state, which scatters light, and a transparent nematic state by an applied electric field and in accordance with one aspect of the present invention an electro-optic device includes in its liquid crystalline material a compound as hereinbefore defined. It will of course be realized that there may be present, a mixture (solution) of compounds as hereinbefore defined and that other compounds exhibiting liquid crystalline behavior may be included. Preferably the mixture of compounds used is a eutectic. The optical effect of the electro-optical device may be enhanced by the inclusion of pleochroic dyes. Suitable pleochroic dyes for this purpose are described in UK patent Ser. Nos. 1,555,954 and 1,555,955.

In accordance with a second aspect of the present invention an electro-optic display device includes as its liquid crystalline material a wide range chiral $S_c$ phase composed of a mixture (solution) of the compounds hereinbefore defined such that the selectivity light reflecting (i.e. colored) chiral $S_c$ phase is converted to a nonlight reflecting, homeotropic (colorless) condition by an applied electric field. That is to say the pitch of the $S_c$ planar structure is effectively unwound by an external electric field which changes the tilt orientation of molecules such that they finally adopt an orthogonal orientation with respect to the layers.

Phases of the present invention exhibit both a chiral $S_c$ phase and a Ch phase at higher temperatures and mixtures of such materials may exhibit thermochromism in both mesophases. This occurs, it is believed, because the helical pitch lengths of the molecular formations are such as to give strongly temperature dependent Bragg reflection of particular wavelengths of light in the visible spectral region. That is, the materials appear colored with a color which varies with the temperature of the material. The ability of a optically active compound to induce helical pitch is measured as the helical twisting power (HTP). The HTP is defined as the pitch of the pure compound measured by extrapolation from a dilute solution (μm) induced by chiral substance. The helical twist in a phase is the greater the smaller the value of the HTP of that substance is. The sequence of colors given with changing temperature in one direction by the cholesteric phase is the reverse of that given by the chiral $S_c$ phase. The materials of the present invention and mixtures thereof may thus be used in surface thermography, e.g., for the detection of breast cancer. They may be applied in a thin film on the surface of interest. The color of the film in reflection at right angles to the surface indicates the temperature of the surface.

This last mentioned property may be used to produce a temperature sensitive display device, e.g. a thermometer, giving a visual display resulting from the effect of changes of temperature upon the helical pitch of the material and consequently the reflected color.

Furthermore this property may be used for cosmetic applications, e.g., for color changing lipsticks, eye-shadows, rouges or make-ups.

The compounds of the formula I are covered by a broad formula of the International Application WO 87/05017 and the European Patent Application EP-0211646. But no compound according to the invention is described there. No one skilled in the art, therefore, could infer how to synthesize these compounds or recognize that they have very small values of the HTP being suitable as additives for thermochromic phases and a extraordinarily high stability against light, especially UV.

Thermochromic phases containing similar compounds are described in the UK Patent Ser. No. 1,592,161 which discloses the (+)-4'-(2methylbutyl)-biphenyl-4-yl ester of (+)-4-(2-methylbutyl)-phenol.

A great disadvantage for many applications of these materials is their low chemical, heat and light, especially UV, stability. The high cost of those chiral compounds is an another adverse property. Because the known compounds possess high HTP values they have to be used in large amounts to induce a helical twist suitable for thermochromic applications. Another adverse property of phases based on these compounds is that high order smectic phases such as, for example, $S_I$, occur at low temperatures, so that the switching time properties are adversely influenced and/or the pitch and/or the tilt and/or the viscosity of the phases do not meet the requirements of display technology.

It has now been found that the compounds of the formula I can substantially reduce the disadvantages mentioned.

The compounds of the formula I are thus outstandingly suitable as components of liquid crystal phases, especially of cholesteric phases. In particular cholesteric phases prepared by the aid of these compounds are chemically stable, have favorable viscosity values, and broad Ch phase ranges.

The compounds of the formula I have a wide range of applications. They can be used as optically active additives which induce the cholesteric phase in a nematic phase, however, it is also possible for compounds of the formula I to be added to liquid crystal base materials from other classes of compounds, for example, in order to vary the dielectric and/or optical anisotropy and/or the viscosity and/or the phase ranges and/or the tilt angle and/or the pitch of such a dielectric.

The invention thus relates to thermochromic liquid crystalline phases with at least two components, characterized in that at least one component is an optically active compound of the formula I, in particular to such phases with two compounds of the formula I wherein the chiral residues $R^1$ and $R^2$ are groups of the formulae II or III

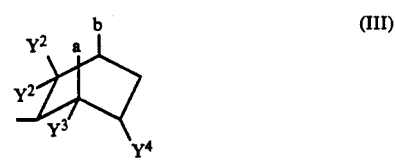

wherein
$R^3$ denotes an optionally substituted aryl or aralkyl group with 6 to 19 C atoms or an alkyl or an alkenyl residue each with up to 16 C atoms, wherein one or two non-adjacent $CH_2$ groups of these residues may be replaced by —O—, —S—, —CO—O— and/or —O—CO—,
$Y^1$ is a normal or branched alkyl group with up to 6 C atoms and is different from $R^3$,
$Y^2$, $Y^3$ and $Y^4$ are each independently H or a normal or branched alkyl group with up to 6 C atoms and
a and b are either H or an alkylene bridging group with 1 or 2 C atoms.

The invention relates furthermore to an electro-optic device containing such a liquid crystalline phase and to a temperature indicating device containing such a liquid crystalline phase.

The invention relates additionally to cosmetic compositions comprising in admixture such a thermochromic liquid crystalline phase and at least one vehicle and, if desired, an auxiliary.

Furthermore the invention relates to the use of such phases in cosmetics, especially in color changing cosmetics.

Eventually the invention relates to a method of surface thermography which includes the step of
(a) applying a thin film of a compound of the formula I or a liquid crystalline phase containing a compound of the formula I to a surface and
(b) observing the color of the film in reflection at, an angle of 90° to the surface.

Partially the compounds of the formula I are known partially they are novel. The invention relates to the novel compounds of the formula I in particular to the compounds of the formula I'

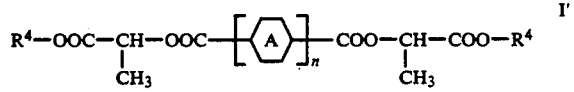

wherein

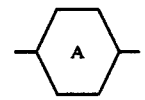

and n have the meaning given and $R^4$ denotes an group with 1 to 15 C atoms.

For simplicity, in the following text, Phe denotes an unsubstituted 1,4-phenylene group and PheX a 1,4-phenylene group substituted by up to four methyl groups and/or halogen atoms.

Preferred compounds of the formula I are those of the part formulae Ia to I

| | |
|---|---|
| $R^1-X^1-Phe-X^2-R^2$ | Ia |
| $R^1-X^1-CO-Phe-CO-X^2-R^2$ | Ib |
| $R^1-X^1-PhePhe-X^2-R^2$ | Ic |
| $R^1-X-CO-PhePhe-CO-X^2-R^2$ | Id |
| $R^1-X^1-PhePhePhe-X^2-R^2$ | Ie |
| $R^1-X^1-CO-PhePhePhe-CO-X^2-R^2$ | If |
| $R^1-X^1-PheX-X^2-R^2$ | Ig |
| $R^1-X^1-CO-PheX-CO-X^2-R^2$ | Ih |
| $R^1-X^1-PhePheX-X^2-R^2$ | Ii |
| $R^1-X^1-CO-PhePheX-CO-X^2-R^2$ | Ij |
| $R^1-X^1-PheXPheX-X^2-R^2$ | Ik |
| $R^1-X^1-CO-PheXPheX-CO-X^2-R^2$ | Il |

In the compounds of the part formulae Ig to Il PheX denotes a 1,4-phenylene group substituted by up to four methyl groups or halogen atoms. Preferred are those compounds wherein PheX denotes a 1,4-phenylene group substituted by one or two halogen atoms. Particularly preferred are compounds wherein PheX denotes a 2-(3-)fluoro-1,4-phenylene group.

In the compounds of the formula I wherein the groups $X^1$ and $X^2$ are directly linked to Phe or PheX, $X^1$ and $X^2$ denote O.

In the compounds of the formula I wherein the groups $X^1$ and $X^2$ are linked to the carbonyl group CO, $X^1$ and $X^2$ denote O or NH.

The compounds of the formula I wherein the groups $R^1$-$X^1$ and $R^2$-$X^2$ are identical are particularly preferred.

The compounds of the part formulae Ia, Ib, Ig and Ih do not show themselves a mesophase, but they impart a tight helical twist into a given nematic or smectic phase without influencing the range of its mesophase too much.

Compounds of the formula I wherein the chiral residues $R^1$ and $R^2$ are groups of the formula II

are preferred.

If $R^3$ is an alkyl radical and/or alkoxy radical, this radical can be straight-chain or branched. Preferably, it is straight-chain and has 2, 3, 4, 5, 6 or 7 C atoms and is accordingly preferably ethyl, propyl, butyl, pentyl, hexyl, heptyl, ethoxy, propoxy, butoxy, pentoxy, hexoxy, or heptoxy, also methyl, octyl, nonyl, decyl, undecyl, dodecyl, tridecyl, tetradecyl, pentadecyl, methoxy, octoxy, nonoxy, decoxy, undecoxy, dodecoxy, tridecoxy or tetradecoxy.

Oxaalkyl is preferably straight-chain 2-oxapropyl (=methoxymethyl), 2-(=ethoxymethyl) or 3-oxabutyl (=2-methoxyethyl), 2-, 3- or 4-oxapentyl, 2-, 3-, 4- or 5-oxahexyl, 2-, 3-, 4-, 5- or 6-oxaheptyl, 2-, 3-, 4-, 5-, 6-, or 7-oxaoctyl, 2-, 3-, 4-, 5-, 6-, 7- or 8-oxanonyl or 2-, 3-, 4-, 5-, 6-, 7-, 8- or 9-oxadecyl.

If $R^3$ is each an alkenyl residue, it can be straight-chain or branched. Preferably, it is straight-chain and has 2 to 10 C atoms. It is accordingly, in particular, vinyl, prop-1- or prop-2-enyl, but-1-, -2- or -3-enyl, pent-1-, -2-, -3- or -4-enyl, hex-1-, -2-, -3-, -4- or -5-enyl, hept-1-, -2-, -3-, -4-, -5- or -6-enyl, oct-1-, -2-, -3-, -4-, -5-, -6- or -7-enyl, non-1-, -2-, -3-, -4-, -5-, -6-, -7- or -8-enyl or dec-1-, -2-, -3-, -4-, -5-, -6-, -7-, -8- or -9-enyl.

Chiral groups of the formula IIa with branched terminal residue $R^3$ can occasionally be of importance because of an improved solubility in the customary liquid crystal base materials.

Branched groups of this type as a rule contain not more than one chain branching. Preferred branched residues $R^3$ are isopropyl, 2-butyl (=1-methylpropyl), isobutyl (=2-methylpropyl), 2-methylbutyl, isopentyl (=3-methylbutyl), 2-methylpentyl, 3-methylpentyl, 2-ethylhexyl, 2-propylpentyl, isopropoxy, 2-methylpropoxy, 2-methylbutoxy, 3-methylbutoxy, 2-methylpentoxy, 3-methylpentoxy, 2-ethylhexoxy, 1-methylhexoxy and 1-methylheptoxy.

Particularly preferred chiral groups of the formula II are those wherein $R^3$ is an alkoxycarbonyl residue. Preferred alkoxycarbonyl groups are methoxycarbonyl, ethoxycarbonyl, propoxycarbonyl, butoxycarbonyl, pentoxycarbonyl, hexoxycarbonyl, heptoxycarbonyl and octoxycarbonyl.

In the compounds of the formula 1 wherein m is O and $R^1$ and/or $R^2$ is a chiral group of the formula II, $R^3$ is preferably an alkyl or an alkenyl residue each with up to 16 C atoms, wherein one or two non-adjacent $CH_2$ groups of these residues are replaced by —O—, —O—CO— and/or —CO—O—.

Preferred chiral groups of the formula II are those of the part formulae IIa to IId

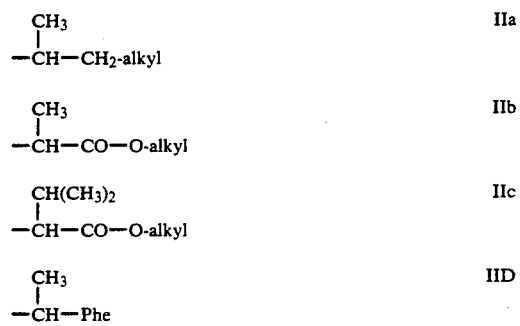

In the chiral groups of the part formulae IIa to IIb alkyl denotes an alkyl group with 1 to 15, preferably 1 to 7 C atoms. In the part formula IIa alkyl with 4 to 7 C atoms are particularly preferred.

In the chiral groups of the part formulae IIa and IIb the group $X^1$ or $X^2$ directly linked to them is preferably O; in IId NH in the meaning of $X^1$ or $X^2$ is preferred.

Compounds of the formula I wherein the chiral residues are a group of the formula III

are preferred.

Preferred chiral groups of the formula III are those of the part formulae IIIa to IIIb

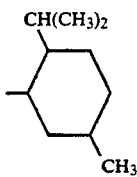

IIIa

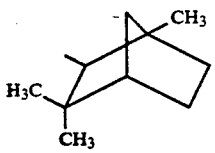

IIIb

The chiral groups of the part formulae IIb to IId, IIIa and IIIb are preferred because they are derived from compounds belonging to the natural chiral pool, for example, from amino acids (IIc from valine), from terpinoids (IIIa from menthol, IIIb from fenchol) or lactic acid (IIb). Therefore, they are derived from cheap starting materials.

Furthermore those cheap, chiral residues impart to the phase according to the invention a tight helical twist. The compounds of the formula I with chiral groups of the preferred part formulae IIa to IId, IIIa and IIIb have an HTP-value of less than 0.14 μm preferably of 0.11 μm to 0.03 μm measured in typical basic host mixtures containing of phenylbenzoates or cyanobiphenyles and cyano-p-terphenyles.

In some cases HTP-values greater than 0.14 μm occur.

Those compounds are used preferably to adjust a selective reflection wavelength of a given thermochromic mixture by adding small amounts to such mixtures.

Particularly preferred are those compounds of the formula I wherein the residue $R^2$ denotes a chiral group of the subformulae IIb, IIc, IIIa or IIIb.

The compounds of the formula I are prepared by methods which are known per se, such as are described in the literature (for example in the standard works, such as Houben-Weyl, Methoden der Organischen Chemie [Methods of Organic Chemistry], Georg-Thieme-Verlag, Stuttgart), and in particular under reaction conditions which are known and suitable for the reactions mentioned in more detail here can also be used in this connection.

If desired, the starting substances can also be formed in situ, such that they are not isolated from the reaction mixture but are immediately reacted further to give the compounds of the formula I.

Esters of the formula I ($m=1/X^1$ and $X^2=O$) can be obtained by esterification of corresponding carboxylic acids (or their reactive derivatives) with alcohols (or their reactive derivatives) preferably the corresponding carboxylic acid and the alcohol are reacted with water absorbing means as, for example, mol sieves or carbodiimides, particularly preferably with dicyclohexylcarbodiimide.

The corresponding carboxylic acids and alcohols are known or can be prepared by processes analogous to known processes.

Particularly suitable reactive derivatives of the carboxylic acids mentioned are the acid halides, above all the chlorides and bromides, and furthermore the anhydrides, for example also mixed anhydrides, preferably those of the corresponding carboxylic acids and trifluoroacetic acid formed in situ by mixing these carboxylic acids with trifluoroacetic anhydride, azides or esters, in particular alkyl esters with 1–4 C atoms in the alkyl group.

Possible reactive derivatives of the alcohols mentioned are, in particular, the corresponding metal alcoholates, preferably of an alkali metal, such as sodium or potassium.

The esterification is advantageously carried out in the presence of an inert solvent. Particularly suitable solvents are ethers, such as diethyl ether, di-n-butyl ether, THF, dioxane or anisole, ketones, such as acetone, butanone or cyclohexanone, amides, such as dimethylformamide or phosphoric acid h-examethyltriamide, hydrocarbons, such as benzene, toluene or xylene, halogenohydrocarbons, such as carbon tetrachloride, dichloromethane or tetrachloroethylene, and sulfoxides, such as dimethylsulfoxide or sulfolane. Water-immiscible solvents can simultaneously be advantageously used for azeotropic distillation of the water formed during the esterification. An excess of an organic base, for example pyridine, quinoline or triethylamine, can occasionally also be used as the solvent for the esterification. An additional, catalytic amount of 4-(N,N-dimethylamino)-pyridine can accelerate the esterification. The esterification can also be carried out in the absence of a solvent, for example by heating the components in the presence of sodium acetate. The reaction temperature is usually between −50° and +250°, preferable between −20° and +80°. At these temperatures, the esterification reactions have as a rule ended after 15 minutes to 48 hours.

In detail, the reaction conditions for the esterification depend largely on the nature of the starting substances used. Thus, a free carboxylic acid is as a rule reacted with a free alcohol or phenol in the presence of a strong acid, for example a mineral acid, such as hydrochloric acid or sulfuric acid. A preferred reaction procedure is the reaction of an acid anhydride or, in particular, an acid chloride with an alcohol, preferably in a basic medium, bases which are of importance being, in particular, alkali metal hydroxides, such as sodium hydroxide or potassium hydroxide, alkali metal carbonates or bicarbonates, such as sodium carbonate, sodium bicarbonate, potassium carbonate or potassium bicarbonate, alkali metal acetates, such as sodium acetate or potassium acetate, alkaline earth metal hydroxides, such as calcium hydroxide, or organic bases, such as triethylamine, pyridine, lutidine, collidine or quinoline. Another preferred embodiment of the esterification comprises first converting the alcohol or phenol into the sodium alcoholate or phenolate or potassium alcoholate or phenolate, for example by treatment with ethanolic sodium hydroxide solution or potassium hydroxide solution, isolating this product and suspending it in acetone or diethyl ether, together with sodium bicarbonate or potassium carbonate, with stirring, and adding a solution of the acid chloride or anhydride in diethyl ether, acetone or diemthylformamide to this suspension, advantageously at temperatures between about −25° and +20°.

Alkoxy compounds of the formula I ($m=0/X^1$ and $X^2$ are O) can be obtained by treating the corresponding optically active alcohol and the corresponding phenol with triphenyl phosphine and diethyl azodicarboxylate as described, for example, by O. Mitsunobu, Synthesis 1981, 1.

Amides of the formula I ($m = 1/X^1$ and $X^2 = NH$) can be obtained by treating the corresponding carboxylic acid (or their reactive derivatives) with amines (or their reactive derivatives).

Particular suitable reactive derivatives of the carboxylic acids mentioned are the acid halids, above all the chlorides and bromides.

The reaction conditions for the preparation of the amides are similiar to those of the esterification.

The thermochromic phases liquid crystalline mixtures according to the invention consist of 3 to 25, preferably 4 to 15, components, at least one of which is a compound of the formula I. The other constitutents are preferably chosen from nematic or nematogenic substances, in particular the known substances, from the classes of azoxybenzenes, benzylideneanilines, biphenyls, terphenyls, phenyl or cyclohexyl benzoates, phenyl or cyclohexyl cyclohexanecarboxylates, phenylcyclohexanes, cyclohexylbiphenyls, cyclohexylcyclohexanes, cyclohexylcyclohexenes, cyclhexylnaphthalenes, 1,4-bis-cyclohexylbenzenes, 4,4'-biscyclohexylbiphenyls, phenyl- or cyclohexylpyrimidines, phenylpyridines, phenyl- or cyclohexyldioxanes, phenyl- or cyclohexyldithianes, 1,2-bis-phenylethanes, 1,2-biscyclohexylethanes, 1-phenyl-2-cyclohexylethanes, optionally halogenated stilbenes, benzyl phenyl ethers, tolanes and substituted cinnamic acids.

The most important compounds which are possible constituents of such liquid crystalline mixtures can be characterized by the formula 1

$$R^4-L-G-E-R^5 \qquad 1$$

wherein L and E are each an unsubstituted or laterally fluoro- or cyano- substituted carbo- or hetero-cyclic ring system from the group comprising 1,4-disubstituted benzene and cyclohexane rings, 1,4-disubstituted 1-cyanocyclohexane rings, 4,4-disubstituted biphenyl, phenylcyclohexane and cyclohexylcyclohexane systems, 2,5-disubstituted naphthalene, di- and tetrahydronaphthalene, quinazoline and tetrahydroquinazoline, G is

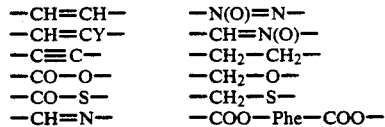

or a C—C single bond, Y is halogen, preferably chlorine, or —CN and $R^4$ and $R^5$ are alkyl, alkoxy, alkanoyloxy or alkoxycarbonyloxy with up to 18, preferably up to 8, carbon atoms, it also being possible for one $CH_2$ group non-adjacent to an oxygen atom to be replaced by —O—, —CH=CH— or —C≡C—, or that one of the radicals $R^3$ and $R^4$ may also denote CN, $NO_2$, $CF_3$, NCS, F, Cl or Br.

In most of these compounds, $R^4$ and $R^5$ are different from one another, one of these radicals usually being an alkyl or alkoxy group. However, other variants of the substituents envisaged can also be used. Many such substances or mixtures thereof are commercially available. All of these substances can be prepared by methods which are known from the literature.

The thermochromic liquid crystalline phases according to the invention contain about 2 to 70, preferably 2 to 50%, of one or more compounds of the formula I. Liquid crystal-line phases which contains 2-80, particular 2-50%, of one or more compounds of the formula I can be used advantageously in the devices according to the invention.

Furthermore the phases according to the invention can be used for cosmetics, preferably for color-changing cosmetics, e.g., for lipsticks, eye-shadows, rouges or make-ups.

Vehicles used for the cosmetic compositions according to the invention ars substances customary for, for example, lipsticks, grease sticks creams, powders and other cosmetics. These are known to the expert or are to be found in standard works, such as, for example, H. Janistyn, Handbuch der Kosmetika und Riechstoffe (Handbook of Cosmetics and Perfumes), Hüthig Verlag Heidelberg.

The liquid crystalline phases according to the invention are prepared in a manner which is customary per se. As a rule, the components are dissolved in one another, preferably at elevated temperature.

The liquid crystalline phases according to the invention can be modified by suitable additives such that they can be used in all the types of liquid crystal display elements disclosed to date.

Such additives are known to the expert and are described in detail in the literature. For example, it is possible to add conductive salts, preferably ethyldimethyldodecylammonium 4-hexyloxybenzoate, tetrabutylammonium tetraphenylboranate or complex salts of crown ethers (compare, for example, I. Haller et al., Mol.Cryst.Liq.Cryst. Volume 24, pages 249-258 (1973)) for improving the conductivity, dichoric dyestuffs for the production of colored guest/host systems or substances for changing the dielectric anisotropy, the viscosity and/or the orientation of the nematic phases. Such substances are described, for example, in German Offenlegungsschrift 2,209,127, 2,240,863, 2,321,632, 2,338,281, 2,450,088, 2,637,430, 2,853,728 and 2,902,177.

The thermochromic cholesteric liquid crystal phases according to the invention are suitable for the thermometry, especially for a good indication of core body temperature in sleeping children and postoperative patients.

Furthermore they can be advantageously applied in the biomedical thermography as an important diagnostic aid for breast cancer detection or placental location.

Beneath mood indicating jewellery U.S. Pat. No. 3,802,945 (1979) and nondestructive testing applications they can be used in atmospheric pollutant detection because of the effect of impurities on the selective reflection wavelength of the liquid crystalline phases according to the invention.

EXAMPLES

The following examples are intended to illustrate the invention without limiting it. Percentages above and below are percentages by weight. All the temperatures are given in degrees Centigrade. The symbols are furthermore as follows: Cr: crystalline solid state, S: smectic phase (the index characterizes the phase type), N: nematic phase, Ch: cholesteric phase, I: isotropic phase. The FIGURE between two symbols indicates the transition temperature.

Example 1

Terephthaloyl chloride (0.0985 m) is dissolved in a mixture of dry dichloromethane (120 ml) and triethylamine (60 ml) at 20° C. To this solution is added a solution of S(—)-ethyl lactate $[[\alpha]^{14} = -10°$ (neat)] (0.197 m)

in dry dichloromethane (60 ml), the reaction mixture is heated under gentle reflux for 2 hours. After cooling, the reaction mixture is washed with dilute hydrochloric acid solution (3×50 ml) and then with water (3×50 ml); the organic layer is dried over magnesium sulphate and evaporated to dryness. Column chromatography, using two weights of silica and two weights of alumina with an eluant mixture of petroleum spirit and dichloromethan in the ratio of 2:1, yields a colorless bis-(S-2-(1-oxo-1-ethoxy)-propyl)terephthaloate as a viscous oil.

Analogously are obtained:
bis-(1R,2S,5R-2-isopropyl-5-methylcyclohexyl) terephthaloate, Cr 77° I
bis-(S-2-methylbutyl) terephthaloate, Cr 7° I
bis-(R-2-octyl) terephthaloate
bis-terephthaloic N-(R-1-phenylethyl)-amide, Cr. 282° I
bis-terephthaloic N-methyl-S-2-(3-methylbutyrate)-amide, Cr 193° I

Example 2

A mixture of dicyclohexylcarbodiimide (0.055 mol) and toluene (15 ml) is given to a mixture of 4,4'-biphenyldicarboxylic acid (0.025 mol, prepared from 4,4'-dibrombiphenyl by reaction with $Cu_2(CN)_2$ in N-methylpyrrolidinone to give 4,4'-dicyanobiphenyl followed by alkaline hydrolysis), R-2-octanol (0.055 mol), 4-dimethylaminopyridine (0.12 g) and toluene (40 ml).

After stirring for 20 hrs at room temperature the reaction mixture is filtered and the filtrate is purified by chromatography on silica gel. After crystallization bis-(R-2-octyl) biphenyl-4,4'-dicarboxylate is obtained as a colorless oil.

Analogously are obtained:
bis-(S-2-(1-oxo-1-ethoxy)-propyl) p-terphenyl-4,4''-dicarboxylate
bis-(1R,2S,5R-2-isopropyl-5-methylcyclohexyl) biphenyl-4,4'-dicarboxylate
bis-(S-2-methylbutyl) biphenyl-4,4'-dicarboxylate

Example 3

A mixture of diethyl azodicarboxylate (0.17 mol) and 100 ml tetrahydrofuran is added to a mixture of biphenyl-4,4'-diole (0.08 mol), S(−)-ethyllactate (0.17 mol) and triphenylphosphine (0.16 mol). The mixture is stirred at 50° C. for 2 h and at 20° C. for 16 h. The solves is evaporated off, the residue is dissolved in hot toluene and cooled to 20° C. The mixture is filtered, evaporated to dryness and chromatographed on silica to give biphenyl-4,4'-dioxy-bis-(ethyl R-2-propionate) as a colorless solid.

Example 4

A mixture of 4,4'-biphenyl-dicarboxylic acid dichloride (0.02 mol/obtained from the dicarboxylic acid (cp. Example 2) and thionyl chlorid), dichlormethane (100 ml), triethylamine (4.6 g) and (S)-(−)-ethyllactate (0.04 mol) is refluxed for 5 hrs. The crude product is isolated, purified by chromatography on silica gel using dichloromethane as eluent followed by crystallization from petroleum spirit to give bis-(S-2-(1-oxo-1-ethoxy)-propyl)-biphenyl-4,4'-dicarbonxylate as a white solid, Cr 66° I.

Example 5

A mixture is formulated containing 90% of a commercially available base mixture (coded E 7 of BDH, Limited) consisting of

| | |
|---|---|
| 51% | 4-cyano-4'-pentylbiphenyl |
| 25% | 4-cyano-4'-heptylbiphenyl |
| 16% | 4-cyano-4'-octyloxybiphenyl |
| 8.0% | 4-cyano-4'-pentyl-p-terphenyl |
| and 10% | bis-(S-2-(1-oxo-2-ethoxy)-propyl terephtaloate |

The clearing point of the host mixture (58° C.) has been depressed to 39° C.

This mixture appears red in reflection at room temperature with a selective reflection wavelength ($\lambda_s$) of 705 nm.

Therefore the pitch length $$(P = \frac{\lambda_s}{RI},$$

with RI=refractive index=1,6) is determined to be 440 nm:

The HTP is determined to be 0.044 μm.

Example 6

A liquid crystal base mixture E7 is doped with different optically active additives: The doped mixtures each contains 10% of the following additives (AI to A7)

| | |
|---|---|
| A1 | Bis-(S-2-methylbutyl) terephthaloate |
| A2 | Bis-(R-2-octyl) terephthaloate |
| A3 | Bis-(1R,2S,5R-2isopropyl-5-methyl-cyclohexyl) terephthaloate |
| A4 | Bis-(S-2-(1-oxo-1-ethoxy)-propyl) terephthaloate |
| A5 | p-(2-Methylbutyl)-phenyl 4'-(2-methylbutyl)-biphenyl-4-yl-carboxylate |
| A6 | 4-Cyano-4'-(2-methylbutyl)-biphenyl |
| A7 | p-(2-Methylbutyl)-phenyl p-decyloxybenzoate |

TABLE I

| HTP (μm) of additives A1 to A7 in Host E7 | | |
|---|---|---|
| | HTP | Twist sense |
| A1 | 0.29 | D |
| A2 | 0.11 | D |
| A3 | 0.11 | L |
| A4 | 0.044 | L |
| A5 | 0.1 | D |
| A6 | 0.14 | D |
| A7 | 0.14 | D |

Table I illustrates the advantage of the inventive compounds A2, A3, A4 to compounds of the prior art (A6, A7). They are advantangeous even compared with A5 which is only to prepare over a sequence of seven preparative steps starting from chiral 2-methylbutanol and, therefore, most expensive.

Example 7

A liquid crystal base mixture (coded ELI-1052 of E. Merck) consisting of
66,7% p-pentylphenyl p-methoxybenzoate
33,3% p-pentylphenyl p-hexyloxybenzoate
is doped with different optically additives. The doped mixture each contains 10% of the corresponding additive.

TABLE II

| HTP (μm) of additives in Host ZLI-1052 | | | |
|---|---|---|---|
| Example | Additive | HTP | Twist sense |
| 7a | A2 | 0.010 | D |
| 7b | A4 | 0.036 | L |
| 7c | A5 | 0.09 | D |

Table II illustrates the advantage of the cheap, inventive compounds (A2, A4) compared with the most expensive compound (A5)

In the mixture of example 7b (10% of A4/90% ZLI 1052) there is a color play:

| Light green/yellow at | 0° C. |
|---|---|
| Orange/yellow | 5° C. |
| Red/orange | 10° C. |
| Red | 15° C. |
| Dark red | 20° C. |

Example 8

A mixture is formulated containing 90% of a commercially available base mixture (coded ZLI-1132 of E. Merck) consisting of
24% of 4-(trans-4-propylcyclohexyl)-benzonitril
36% of 4-(trans-4-pentylcyclohexyl)-benzonitril
25% of 4-(trans-4-heptylcyclohexyl)-benzonitril
15% of 4'-cyano-4-(trans-4-pentylcyclohexyl)biphenyl
and 10% of bis-(S-2-(1-oxo-2-ethoxy)-propyl) terephthaloate exhibits a clearing point of 43° C. The HTP is determined to be 0.036 μm.

Example 9

A mixture is formulated containing 90% of a commercially available base mixture (coded ZLI-1895 of E. Merck) consisting of
28% of 4'-cyano-4-ethylbicyclohexyl
19% of 4'-cyano-4-propylbicyclohexyl
23% of 4'-cyano-4-butylbicyclohexyl
30% of 4'-cyano-4-heptylbicyclohexyl
and 10% of bis-(S-2-(1-oxo-1-ethoxy)-propyl)terephthaloate
exhibits a clearing point of 49° C. The HTP is determined to be 0.039 μm.

Example 10

A mixture is formulated containing 90% of a commercially base mixture (coded E8 of BDH, Limited) consisting of
43% of 4-cyano-4'-pentylbiphenyl
17% of 4-cyano-4'-propyloxybiphenyl
13% of 4-cyano-4'-pentyloxybiphenyl
17% of 4-cyano-4'-octyloxybiphenyl and
10% of 4-cyano-4''-pentyl-p-terphenyl
and 10% of bis-(S-2-(1-oxo-1-ethoxy)-propyl)-4,4'-biphenyldicarboxylate (of Example 4) the clearing point of the host mixture (71° C.) has been depressed to 61,6° C. This mixture appears red in reflection at room temperature with a selective reflection wavelength ($\lambda_s$) of 700 nm. The pitch length (P) is determined to be 437 nm. The HTP is determined to be 0.0437 μm.

Example 11

A liquid crystal mixture is formulated containing 90% of ZLI-1052 (cp. Example 7) and 10% of bis-(S-2-(1-oxo-1-ethoxy)-propyl)-4,4'-biphenyldicarboxylate.

The clearing point of the host mixture (48° C.) has been depressed to 38,8° C.

The mixture appears:

| Purple at | −20° C. |
|---|---|
| Dark blue | −1.5° C. |
| Light blue | 19.5° C. |
| Turquoise | 28.1° C. |

Example 12

The cholesteric liquid crystalline mixtures of the examples 5 to 11 are admixed to customary vehicles to achieve cosmetic compositions with attractive colored effects and pleasant skin feeling.

We claim:

1. A thermochromic liquid crystalline composition comprising at least two components wherein at least one of said two components is an optically active compound of the formula

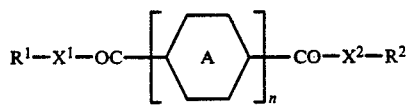

wherein
R$^1$ and R$^2$ are each independently groups of formulae II or III

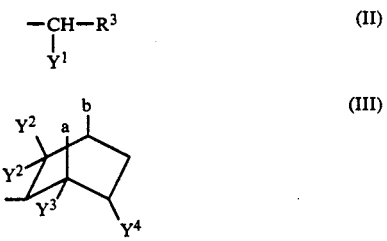

wherein
R$^3$ is a substituted or unsubstituted aryl or aralkyl residue with 6 to 19 C atoms or an alkyl or an alkenyl residue, each with up to 16 C atoms, wherein one or two non-adjacent CH$_2$ groups of these residues may be replaced by —O—, —S—, —CO—O—, and/or —O—CO—;
Y$^1$ is a normal or branched alkyl group with up to 6 C atoms and is different from R$^3$;
Y$^2$, Y$^3$, and Y$^4$ are each independently H or a normal or branched alkyl group with up to 6 C atoms; and
a and b are either H or an alkylene bridging group with 1 or 2 C atoms;

denotes a 1,4-phenylene group optionally substituted by fluorine;
X$^1$ and X$^2$ are each independently O or NH; and
n is 1, 2 or 3,
the other of said at least two components comprises at least one liquid crystal compound.

2. A phase according to claim 1, wherein m denotes 1.

3. A composition according to claim 1, wherein the groups $R^1$-$X^1$ and $R^2$-$X^2$ are identical.

4. A compound of the formula I'

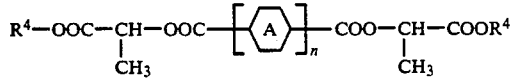 I' wherein

is a 1,4-phenylene group optionally substituted by fluorine, n is 1, 2, or 3, and $R^4$ is a normal or branched alkyl residue with 1 to 15 C atoms.

5. A liquid crystalline composition according to claim 1, wherein said phase contains at least two optically active compounds of Formula I and wherein said chiral residues $R^1$ and $R^2$ are of subformula II or III $$-CH-R^3 \atop Y^1 \qquad (II)$$

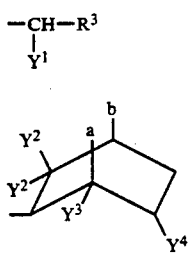 (III)

wherein $R^3$ is a substituted or unsubstituted aryl or aralkyl group with 6 to 19 C atoms or an alkyl or an alkenyl residue each with up to 16 C atoms, wherein one or two non-adjacent $CH_2$ groups of these residues can be replaced by —O—, —S—, —CO—O—, and/or —O—CO;

$Y^1$ is a normal or branched alkyl group with up to 6 C atoms and is different from $R^3$;

$Y^2$, $Y^3$, and $Y^4$ are each independently H or a normal or branched alkyl group with up to 6 C atoms; and a and b are each H or together form an alkylene bridging group having 1-2 C atoms.

6. A liquid crystalline composition according to claim 1 wherein said optically active compound is of the formula I'

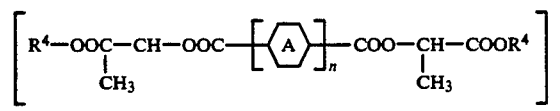

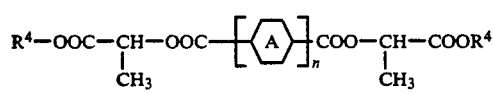

wherein

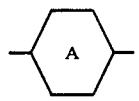

is a 1,4-phenylene group optionally substituted by fluorine, n is 1, 2 or 3, and $R^4$ is an alkyl group having 1-15 C atoms.

7. A liquid crystalline composition according to claim 1, wherein said optically active compound is of the formula

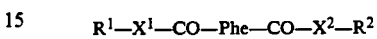 (Ib)

wherein Phe is an unsubstituted 1,4-phenylene group.

8. A liquid crystalline composition according to claim 1, wherein said optically active compound is of the formula

 (Id)

wherein Phe is an unsubstituted 1,4-phenylene group.

9. A liquid crystalline composition according to claim 1, wherein said optically active compound is of the formula

 (If)

wherein Phe is an unsubstituted 1,4-phenylene group.

10. A liquid crystalline composition according to claim 1, wherein the groups $R^1$—$X^1$ and $R^2$—$X^2$ are identical.

11. A liquid crystalline composition according to claim 1, wherein chiral residues $R^1$ and $R^2$ are of the following formulae

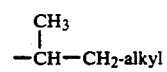 IIa

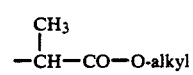 IIb

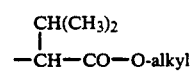 IIc

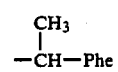 IId

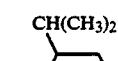

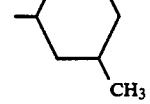 IIIa

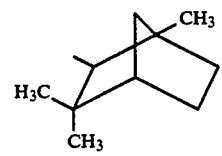 IIIb

12. A liquid crystalline composition according to claim 1, wherein the thermochromic phase is a cholesteric phase.

13. A liquid crystalline composition according to claim 1, wherein the thermochromic phase is a chiral smectic C phase.

14. A liquid crystalline composition according to claim 1, wherein said composition exhibits both a thermochromic cholesteric phase and a thermochromic chiral smectic C phase.

15. A method of inducing a cholesteric phase and a chiral smectic C phase underlying said cholesteric phase to a liquid crystalline composition possessing a nematic or smectic C phase, said method comprising adding to said liquid crystalline composition a chiral compound of formula I

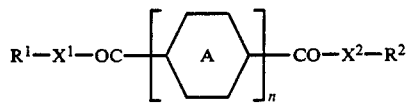

$R^1$ and $R^2$ are each independently a chiral residue, imparting to the phase a tight helical twist

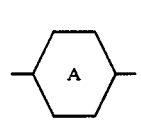

denotes a 1,4-phenylene group optionally substituted by fluorine, $X^1$ and $X^2$ are each independently O or NH, and n is 1, 2 or 3.

16. A liquid crystalline composition in accordance with claim 1, wherein said at least one compound of formula I exhibits a helical twisting power with respect to said composition of less than 0.14 microns.

17. A liquid crystalline composition in accordance with claim 1, wherein said at least one compound of formula I exhibits a helical twisting power with respect to said composition of less than 0.03-0.11 microns.

18. A liquid crystalline composition according to claim 1, wherein said composition contains 2-70% of one or more compounds of formula I.

19. A liquid crystalline composition according to claim 1, wherein said composition contains 2-50% of one or more compounds of formula I.

20. A liquid crystalline composition according to claim 1, wherein $X^1$ is NH.

21. A liquid crystalline composition according to claim 1, wherein $X^2$ is NH.

22. A liquid crystalline composition according to claim 20, wherein $X^2$ is NH.

23. A liquid crystalline composition according to claim 1, wherein n is 1.

* * * * *

UNITED STATES PATENT AND TRADEMARK OFFICE
CERTIFICATE OF CORRECTION

PATENT NO. : 5,188,815
DATED : February 23, 1993
INVENTOR(S) : David Coates, et. al.

It is certified that error appears in the above-indentified patent and that said Letters Patent is hereby corrected as shown below:

Column 14, Claim 2, line 68, change "phase" to read -- Composition --.

Signed and Sealed this

Nineteenth Day of July, 1994

*Attest:*

BRUCE LEHMAN

*Attesting Officer*  *Commissioner of Patents and Trademarks*